United States Patent [19]

Mixan et al.

[11] 4,057,517
[45] Nov. 8, 1977

[54] SYNTHETIC RESIN FUNGICIDAL PAINT COMPRISING 1,3-DITHIOLO-(4,5-B)PYRAZIN-2-YLIDENE-PROPANEDINITRILE 4-OXIDE

[75] Inventors: Craig E. Mixan; Christian T. Goralski; R. Garth Pews, all of Midland, Mich.

[73] Assignee: The Dow Chemical Company, Midland, Mich.

[21] Appl. No.: 740,632

[22] Filed: Nov. 10, 1976

Related U.S. Application Data

[62] Division of Ser. No. 649,175, Jan. 15, 1976.

[51] Int. Cl.$^2$ .............................................. C08L 91/00
[52] U.S. Cl. ............................. 260/22 R; 260/29.2 E; 260/29.6 R; 260/16; 260/17 R; 260/30.6 R; 260/75 R; 260/873; 260/901; 428/541; 260/2 EP; 260/13; 260/77
[58] Field of Search ................ 260/250 BN, 13, 2 EP, 260/17 R, 77.5 AP, 30.6 R, 22 R, 75 R, 29.2 E, 29.6 R, 16; 424/250

[56]  References Cited
U.S. PATENT DOCUMENTS

| 2,493,071 | 1/1950 | Kendall | 260/327 |
| 3,048,596 | 5/1962 | Hatchard | 260/302 F |
| 3,291,802 | 12/1966 | Collins | 260/250 |
| 3,825,548 | 7/1974 | Kurihara | 260/294.8 B |

FOREIGN PATENT DOCUMENTS 7,437,248   1974   Japan.

OTHER PUBLICATIONS

J. Am. Chem. Soc. vol. 84, pp. 4746–4747, 1962, Simmons et al.
J. Pharmaceutical Sciences, vol. 57, pp. 1611–1613, (1968), Foye et al.

Primary Examiner—Edward M. Woodberry
Attorney, Agent, or Firm—Daniel L. DeJoseph

[57] ABSTRACT

The new compound 1,3-dithiolo(4,5-b)pyrazin-2-ylidene-propanedinitrile 4-oxide is prepared by reacting substantially equimolar proportions of di-(sodiomercapto)methyleneamalononitrile with 2,3-dichloropyrazine 1-oxide. The compound has fungicidal, algicidal and marine antifoulant utility.

2 Claims, No Drawings

SYNTHETIC RESIN FUNGICIDAL PAINT COMPRISING 1,3-DITHIOLO-(4,5-b)PYRAZIN-2-YLIDENE-PROPANEDINITRILE 4-OXIDE

This is a division of application Ser. No. 649,175 filed Jan. 15, 1976.

BACKGROUND OF THE INVENTION

The art has long sought a compound or compounds which would have fungicidal, algicidal and marine antifoulant activity at relatively low concentration levels and also sufficiently low water solubility at useful levels as to be effective for long periods of time without being leached out by water or rain. The compound 1,3-dithiolo(4,5-b)pyrazin-2-ylidene-propanedinitrile 4-oxide has such a desirable combination of properties. Hereinafter such compound will be referred to as "Compound".

SUMMARY OF THE INVENTION

This invention concerns novel Compound. Compound is prepared by reacting a di-(alkali metal mercapto)methylene-malononitrile, (the sodium and potassium salts are most conveniently used), advantageously dissolved in an inert organic solvent such as dimethylsulfoxide, acetonitrile or dimethylformamide, and preferably the last named, with a substantially equimolar proportion of 2,3-dichloropyrazine 1-oxide, also advantageously dissolved in an inert organic solvent such as dimethylsulfoxide, acetonitrile or dimethylformamide, of which the last is preferred. The reaction mixture is stirred at a temperature ranging between about 20° and about 50° C., and preferably at about 45° to about 50° C. until reaction is substantially completed. The time of reaction varies from about 48 hours at 20° C. to about 16 hours or less at the preferred temperature range. Upon conclusion of the reaction, the reaction mixture is poured into ice water. A yellow solid develops and is collected by suction filtration. The crude product is dried and recrystallized from chloroform to give Compound as a yellow-orange solid, melting at 224°-245° C. Compound has a partition coefficient of 8.05 (octanol/water), indicating that it is ecologically safe in terms of bioconcentration in the environment. Compound has fungicidal, alficidal and marine antifoulant activity. Said compound has the formula:

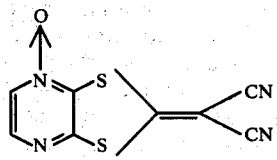

DESCRIPTION OF SOME PREFERRED EMBODIMENTS

The following examples and teachings additionally describe specific embodiments and the best mode contemplated by the inventor of carrying out the invention.

EXAMPLE 1: Preparation of Compound

To a stirred solution of 7.4 g. (0.04 mole) of di-(sodiomercapto)methylenemalononitrile in 70 ml. dimethylformamide (DMF) is gradually added 6.6 g. (0.04 mole) 2,3-dichloropyrazine 1-oxide in 70 ml. DMF. The mixture is stirred at 45°-50° C. for 16 hrs. and thereafter is poured into 500 ml. ice water. A yellow solid develops and is collected by suction filtration. The crude product is dried and recrystallized from chloroform to give 5.45 g. yellow-orange solid (58 percent), melting at 244°-245° C.

Anal. Calcd. for $C_8H_2N_4OS_2$, percent: C. 41.03; H, 0.85; N, 23.93; S, 27.35. Found: C, 40.9; H, 1.07; N, 24.08; S, 27.3.

EXAMPLE 2: Fungicidal Activity

Compound has fungicidal activity. In testing for fungicidal activity using conventional agar inhibition tests, 100 percent inhibition was obtained against the following organisms at the indicated concentrations, given in parts per million (ppm): *C. albicans*, less than one; *T. mentagrophytes*, less than one; *C. pelliculosa*, 10; *P. pullulans*, 10; *Ceratocystis ips*, less than one; Trichoderma species P-42, less than one, *R. nigricans*, 10; and *A. niger*, 10.

EXAMPLE 3: Algicidal Activity

Compound is also algicidal. In a screening test against Enteromorpha zoospores, fronds of Enteromorpha were collected and air dried for a period of 24 hrs. to stress them. They were then immersed in millipore-filtered sea water with a salinity of 20.20 ppt (parts per thousand) at a temperature of 23° C, contained in a 1500 ml. beaker. The weight of the dried fronds was 8.3 g. After 24 hrs., the fronds were removed and a sufficient amount of filtered sea water was added to bring the total volume to 1500 ml. An algal nutrient, Murphy's Instant Ocean (MIO), was added in the amount of 3.60 ml. nutrient per 1500 ml. algal culture. MIO contains relative proportions of 100 ppm $KNO_3$, 1.0 ppm EDTA (ethylene-diamine tetraacetic acid), 10 ppm Fe, $1.0 \times 10^{-3}$ ppm vitamin $B_{12}$, 0.1 ppm thiamine and 10 ppm $PO_4$. The final concentration of spores was approximately $3.5 \times 10^{-3}$/ml. The screening test was run for 14 days at 23° C. at concentrations of Compound logarithmically spaced from 0.01 ppm to 1.0 ppm. At the end of the 14-day period, the nutrient media having a concentration of 1.0 ppm Compound showed no living algal growth. At 0.32 ppm Compound, growth was present but stunted, i.e., sparse growth having a greenish-yellow color as compared with the bright vivid green in the control. At concentrations of 0.1-0.01 ppm Compound, growth was present and abundant, comparable to the controls. Similar results were obtained with diatoms and other algae.

EXAMPLE 4: Marine Antifoulant Activity

Compound is also effective in controlling marine foulants and organisms such as barnacles and Limnoria. The physiological effect of Compound on barnacles was monitored and contrasted with the well-known antifoulant, tributyl tin oxide. The activity of Compound against barnacles was tested by observing the physiological effect it had on the rhythmic pacemaker-controlled pumping activity, which serves to move water in and out of the barnacle. This is a feeding and respiratory activity. This activity was monitored with a motion transducer. The response to Compound was ascertained very readily. At first, the pumping activity increased, then it became irregular and after an hour had passed, it ceased. The barnacles were dead. The time, cause and effect were quite similar to the well-known antifoulant, tributyl tin oxide. The barnacles so observed were obtained by placing plastic slides in a sea water canal where fouling was allowed to take place. The slides were left in the water until 20 to 100 barnacle cyprids were attached to the surface. This took from 1 to 7 days. The number of cyprids present in the plankton naturally varied from day to day. Excess material such as dirt on the slides was removed and the slides containing the cyprids and newly metamorphosed barnacles were placed in a series of beakers containing different concentrations of Compound, exposed therein for 24 hours and observed until death of the barnacles. In the test reported, the concentration of Compound was 8.0 ppm in sea water. Final readings were made two days after exposure. In the interim, the slides were kept in troughs of running sea water.

Compound is also effective in marine antifoulant paints. Particularly preferred are those having a vinyl resin binder such as, for example, a plasticized polyvinyl chloride or a polyvinyl chloride-polyvinyl acetate type. Advantageously the binders are formulated as latexes or emulsions. In the finished paints, amounts of Compound from about 1 to about 25 weight percent are advantageously used, and amounts from about 10 to about 25 weight percent of Compound are preferred. The following paint formulation is representative. The proportions given are in weight parts.

EXAMPLE 5: White Marine Antifoulant Paint

| | |
|---|---|
| Compound | 23.6 |
| Titanium dioxide | 11.0 |
| Bentone bentonite | 0.9 |
| Trixylyl phosphate plasticizer | 2.8 |
| Vinyl resin VAGH | 8.5 |
| Rosin | 5.7 |
| Methyl isoamyl ketone | 23.75 |
| Xylol (high flash) | 23.75 |
| | 100.00 |

The vinyl resin, rosin, plasticizer and solvents are mixed together in a paint mixer and when a uniform dispersion is obtained the bentonite, titanium dioxide and Compound are thereafter added to the vehicle with mixing to give a uniform dispersion having a solids content of approximately 39.75%. In use, at least 2 coats at 50 microns (2 mils) per coat are used on an appropriate substrate before exposure to a marine environment which normally gives rise to fouling with marine organisms.

In addition to vinyl resin binder paints, epoxy and polyurethane binder paints containing Compound are also useful as marine antifoulant coatings. Coatings and films therefrom remain substantially free from build up of marine organisms for periods ranging from about 3 to about 12 months, depending upon the concentration of Compound and the thickness of the applied coating or film. Obviously, substantially water-insoluble binders are used in marine antifoulant paints.

Wood impregnated with about 1 to about 5 weight percent Compound and preferably from about 2 to about 5 weight percent compound, advantageously in combination with one or more adjuvants such as a penetrating carrier vehicle, a water-resistant binding material, a surfactant or an inert finely divided solid, gives a product which is resistant and cidal to marine organisms which would otherwise be harmful to wood. The following example is representative.

EXAMPLE 6: Limnoria-Resistant Wood

In controlling marine-boring organisms of the order Isopoda and class Crustacea, such as Limnoria, wooden blocks of clear southern yellow pine, ½ in. (1.27 cm.) by 1 in. (2.54 cm) by 2 in. (5.08 cm.) were vacuum-pressure impregnated, pursuant to the method described in Ballard et al., U.S. Pat. No. 3,279,984, with a 10% by weight dispersion of Compound in creosote heated to about 190° F. (87.8° C.). The wood specimens were fully immersed in the treating dispersion to give a retention (average of two blocks) of 14.15 pounds per cubic foot (226.65 kg./m.$^3$) of dispersion or 2.1 weight percent of compound. Control specimens impregnated with creosote only under otherwise similar conditions were also prepared. The specimens were exposed to Limnoria attack in flowing sea water in a sea water flume in an area where Limnoria are prevalent. The specimens were periodically inspected over a period of 1 year. The controls impregnated with creosote only exhibited heavy attack by Limnoria at the end of the year, while the specimens impregnated with Compound in creosote were completely free from Limnoria attack.

EXAMPLE 7: Wood Preservation

Compound is also useful as a wood preservative. In a field stake test wherein Compound was compared with penta-chlorophenol for wood preservative effectiveness, the following procedure was used. Southern yellow pine sapwood stakes ¾ in. (1.90 cm.) × ¾ in. (1.90 cm.) × 18 in. (45.72) were treated with methylene chloride solutions of the compounds. In the solutions of Compound, 1.0 weight percent dimethylformamide was used as a booster solvent. Stakes were separated according to density and finally chosen for inclusion in such a way as to minimize the density range within the test. Treating was accomplished with a full cell, vacuum-pressure procedure. Fourteen stakes were included in each treatment, thereby allowing a choice of 10 stakes most centrally located within the retention range for ultimate field installation. The treating cycle included 30 minutes' exposure at 28 in. of vacuum, admission of treating solution while specimens were held submerged and while vacuum was maintained, followed by 200 psi nitrogen pressure for 30 minutes. Stakes were weighed before and after treatment and the pick-up used to calculate the retention of total toxicants. Stakes were then open-staked in laboratory hoods until essentially all of the methylene chloride had evaporated, as determined by weight.

The identity of the field stakes, average retentions, coefficients of variation and average index of condition after 9 months of exposure in Florida in a light sandy soil wherein the stakes were subjected to severe termite and fungal attack are presented in the following table.

TABLE I

| Preservative | Ave. Retention | | Coeff. of Variation | Ave. Index of Condition* |
|---|---|---|---|---|
| Compound | 0.0050 lb./ft.$^3$ | (.08 kg/m.$^3$) | 1.3% | 7.3 |
| | 0.020 | (.32) | 2.1 | 9.1 |
| | 0.12 | (1.92) | 1.6 | 10.0 |
| Pentachlorophenol tech. | 0.10 | (1.6) | 2.9 | 8.8 |
| | 0.20 | (2.3) | 2.0 | 10.0 |
| | 0.40 | (6.41) | 1.0 | 9.9 |
| | 0.61 | (9.77) | 1.0 | 9.9 |

TABLE I-continued

| Preservative | Ave. Retention | Coeff. of Variation | Ave. Index of Condition* |
| --- | --- | --- | --- |
| Solvent control | | | 4.3 |
| Untreated control | | | 7.1 |

*10 = Sound (no termite or fungal attack)
9 = Trace of fungal decay or termite attack or both
7 = Moderate fungal decay or termite attack or both
4 = Heavy fungal decay or termite attack or both
0 = Failure due to fungal decay or termite attack or both (i.e., slight force causes breakage of stake).
The test procedure and evaluation was pursuant to ASTM Standard Method D1758-62.

Compound is also useful in preparing paints which are resistant to fungas growth. An amount of compound ranging between about 0.25 and about 5.0 weight percent is used, depending upon the type of exposure. Representative binders for such fungus-resistant paints are the acrylates, alkyd-modified arcrylates, polyvinyl acetate-acrylates, alkyds and oil-modified alkyds. Advantageously, emulsion and latex-type binders are most used because of the importance of the do-it-yourself market. The following example is a typical formulation.

EXAMPLE 8: White Fungas-Resistant Paint

| | Lbs. | (Kg.) | Gals. | (L.) |
| --- | --- | --- | --- | --- |
| Water | 60.3 | (27.35) | 7.24 | (27.41) |
| Ethylene glycol | 30.0 | (13.68) | 3.22 | (12.19) |
| Hydroxyethyl methyl cellulose, aqueous 2.5%, 1.0 average methoxy substitution, 2.5 average hydroxyethyl substitution | 80.0 | (36.29) | 9.75 | (36.90) |
| Tamol 850 (30%), Na salt of polycarboxylic acid, dispersant | 8.5 | (3.86) | 0.85 | (3.22) |
| Compound | 41.72 | (18.69) | 4 | (15.14) |
| Nopco NDW nonionic antifoamer | 1.0 | (.45) | 0.13 | (.49) |
| Rutile TiO$_2$ (non-chalking) | 150.0 | (68.0) | 4.56 | (17.26) |
| Calcium carbonate | 125.1 | (56.75) | 5.68 | (21.50) |
| The above are ground in a high speed mill for 10–15 minutes, then let down at a slower speed with the following: | | | | |
| Rhoplex AC-388 (50%) alkyd-modified acrylic latex | 498.9 | (226.3) | 56.68 | (214.55) |
| Antifoamer (as above) | 1.0 | (.45) | 0.13 | (0.49) |
| Pine oil | 10.0 | (4.54) | 1.08 | (4.09) |
| Propylene glycol | 30.0 | (13.61) | 3.23 | (12.23) |
| Water or hydroxyethyl methyl cellulose (as above) | 48.1 | (21.82) | 5.84 | (22.11) |
| | 1084.62 | (491.97) | 102.39 | (387.58) |

A control paint was similarly prepared, omitting Compound.

Test specimens of clear ponderosa pine boards, 6 in. (15.24 cm.) by 3 ft. (0.91 m.) were similarly primed with an unpreserved alkyd primer and thereafter half of the test boards were coated with the control paint and half with the fungus-resistant paint applied with a drawdown bar set to leave a 10 mil (.0254 mm.) film. After air drying, the boards were exposed outdoors in Freeport, Tex., which has a warm, humid climate where fungus growth is prevalent. The test boards were examined after 5 months, at which time the controls were covered with fungus and the protected boards were fungus free. After 10 months, the boards coated with the fungus-resistant paint were still fungus free. No further examinations were made.

Preparation of Starting Materials

The preparation of di(alkalimercapto)methylenemalononitriles is disclosed in J. Org. Chem. 29,663 (1964). Also see U.S. Pat. No. 2,493,071, J. D. Kendall and H. D. Edwards, 1950.

2,3-Dichloropyrazine 1-oxide

To a stirred solution of 750 g. (5 mol) of 2,3-dichloropyrazine* in 5 l. of sulfuric acid at 10° C, is gradually added 1,500 g. (5.5 mol) of potassium persulfate. The reaction mixture is stirred at room temperature for 24 hours and carefully poured into 19 l. of ice water. The aqueous solution is extracted with chloroform and the extract is washed with sat. NaHCO$_3$ and sat. NaCl solutions and dried over MgSO$_4$. Evaporation of the solvent provides 698 g. (85%) of white solid. MP 101–103° C. (lit. MP 104°–106° C). This material is used without further purification.

*Prepared by the method of U.S. Pat. No. 3,291,802.

The inventors, in accordance with the dictates of good product stewardship, point out that Compound should be handled with care as with other known and useful chemical irritants since it is a severe eye irritant and a moderate skin irritant. The starting material, 2,3-dichloropyrazine 1-oxide, should also be handled with care since it is a severe skin irritant which can cause a chemical burn.

What is claimed is:

1. A fungicidal paint comprising a substantially water-insoluble synthetic resinous binder selected from the group consisting of acrylates, alkyd-modified acrylates, polyvinyl acetate-acrylate copolymer, alkyds and oil-modified alkyds in combination with from about 0.25 to about 5 weight percent of 1,3-dithiolo (4,5-b) pyrazine-2-ylidene-propanedinitrile 4-oxide.

2. A substantially water-insoluble synthetic resinous film selected from the group consisting of acrylate resin film, alkyd-modified acrylate resin film, polyvinylacetate-acrylate resin film, alkyd resin film and oil-modified alkyd resin film comprising a fungicidal amount of 1,3,-dithiolo(4,5-b) pyrazin-2-ylidene-propanedinitrile 4-oxide.

* * * * *